United States Patent [19]

Mascuch et al.

[11] Patent Number: 4,796,637

[45] Date of Patent: Jan. 10, 1989

[54] RADIOPAQUE MARKER FOR STEREOTAXIC CATHETER

[75] Inventors: Frank Mascuch, Watchung; Arthur Winter, Short Hills, both of N.J.

[73] Assignee: Victory Engineering Company, Springfield, N.J.

[21] Appl. No.: 62,967

[22] Filed: Jun. 17, 1987

[51] Int. Cl.⁴ .................................... A61M 25/00
[52] U.S. Cl. ............................. 128/658; 604/280
[58] Field of Search .............. 128/657, 658, 772; 604/280

[56] References Cited

U.S. PATENT DOCUMENTS

| | | | |
|---|---|---|---|
| 3,605,750 | 9/1971 | Sheridan et al. | 604/280 X |
| 4,577,637 | 3/1986 | Mueller, Jr. | 128/658 |
| 4,657,024 | 4/1987 | Coneys | 128/658 |

FOREIGN PATENT DOCUMENTS

| | | | |
|---|---|---|---|
| 0014424 | 8/1980 | European Pat. Off. | 128/772 |
| 0094480 | 8/1978 | Japan | 604/280 |

Primary Examiner—Lee S. Cohen
Attorney, Agent, or Firm—Thomas R. Morrison

[57] ABSTRACT

A stereotaxic catheter includes at least one lumen parallel to an axis thereof. The lumen includes a staff having disposed thereon or therein a predetermined number of spaced-apart markings of a radiopaque material. In a preferred embodiment, the markings are equidistantly spaced circumferential bands of a material having a large X-ray signature. The lumen containing the staff is preferably sealed at both ends and is most preferably sealed in close adjacency to each end of the staff whereby the staff is retained in a stable and predictable positional releationship to the remainder of the catheter.

5 Claims, 2 Drawing Sheets

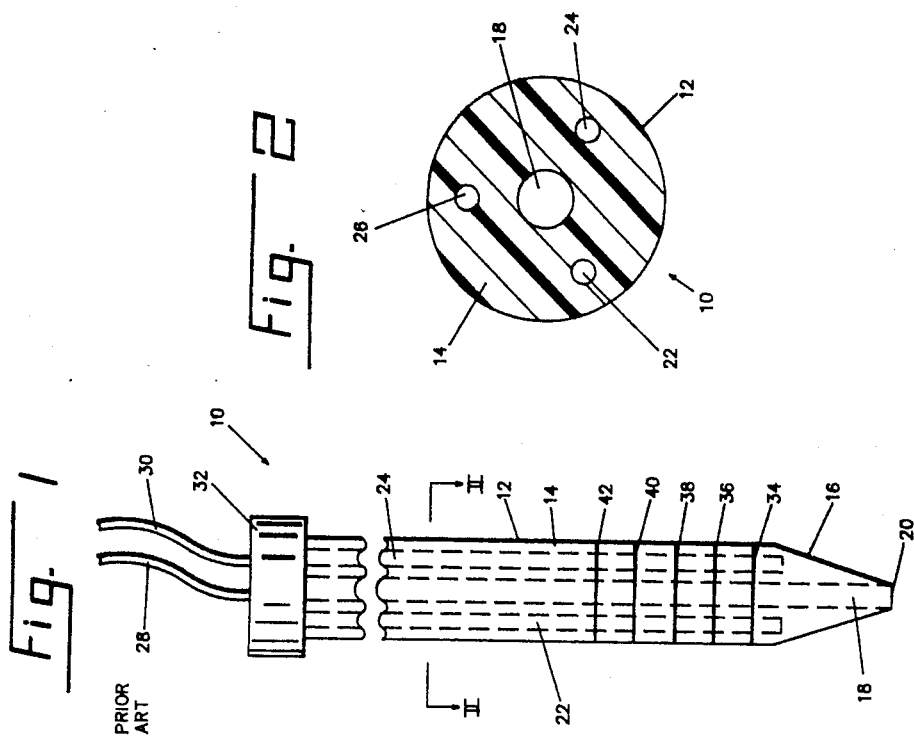

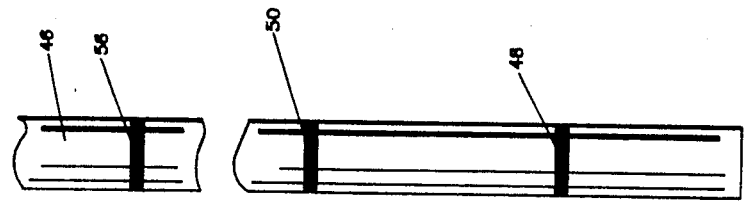
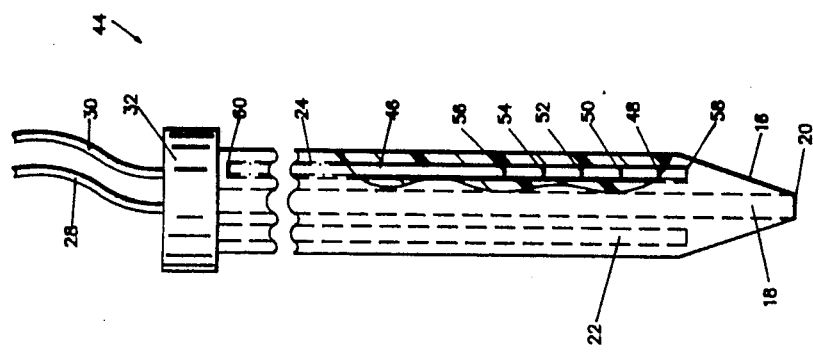

RADIOPAQUE MARKER FOR STEREOTAXIC CATHETER

BACKGROUND OF THE INVENTION

The present invention relates to medical devices and, more particularly, to medical devices employed for indicating a position of a device located within a body and being imaged on an X-ray imaging system.

A stereotaxic catheter is employed, for example, to penetrate the brain of a human being for local administration of an anti-cancer drug or cancer destroying radiation. Such a use is described in allowed U.S. patent application Ser. No. 779,285, now matured into U.S. Pat. No. 4,681,122, wherein a multi-lumen catheter includes a microwave antenna in one of the lumens for elevating the temperature of tissue surrounding the antenna. A temperature sensor in a second of the lumens senses the tissue temperature to permit temperature control with a precision effective to damage cancerous tissue without excessive damage to healthy tissue.

The catheter, and particularly the microwave antenna and temperature sensor within the catheter, must be positioned precisely within the tissue in order to localize the hyperthermic effect of the microwave radiation. Precise angular positioning of a catheter is aided by a positioning device such as a stereotaxic array plug disclosed in U.S. Pat. No. 4,629,451. In this device, a plug is threaded into an opening in a patient's skull. The plug, supports guide holes for guiding the insertion into the brain of a catheter at precise angles. A radiopaque marking pattern on the outer surface of the plug provides a calibration pattern on an X-ray image.

Longitudinal positioning of the catheter in the brain is preferably aided by an X-ray image, whereby a practitioner may see the relationship between the catheter and the portion of the brain requiring treatment. The catheter itself is generally made of a resin such as, for example, a silicone plastic, which does not present substantial X-ray absorption. Thus, means are required to enhance the visibility of the catheter on an X-ray image.

One technique for enhancing the visibility of the catheter, disclosed in the referenced allowed U.S. patent application, includes placing one or more radiopaque marking bands about the surface of the catheter. In a preferred embodiment, a pattern of equally spaced bands about the catheter are spaced a predetermined distance apart along the catheter axis. The spacing, and the known relationship between the locations of the bands and the microwave antenna, provides a practitioner viewing an X-ray image displaying the bands with the information required to permit precise longitudinal positioning of the catheter.

The bands are conventionally formed using a liquid containing a non-toxic material having a large X-ray signature. The liquid is applied in a series of stripes, about the circumference of the catheter and then dried. One type of radiopaque marking material found satisfactory from the standpoint of its X-ray signature is a gold powder mixed with a silicone adhesive to form a paste. Other compositions having the required properties of X-ray signature and non-toxicity may be employed. One such composition is Tantalum Powder-Type 268/1905 ZM-414 (−325 Mesh size) distributed by Fansteel Metals.

Silicone rubber is selected as the material for catheters at least partly because such material rejects the attachment of contaminants to its surface. Although desirable from the standpoint of therapy, such a property makes the surface of a catheter a poor host for radiopaque marking bands. Thus, during insertion of a catheter into brain tissue, and its later removal therefrom, a substantial likelihood exists that some of the marking material may rub off and remain in the tissue. It is, of course, undesirable to permit the deposit of a foreign material within brain tissue. In addition, if a substantial part of the marking bands are removed during insertion, their visibility on an X-ray image may be degraded.

One possibility may be to form annular grooves in the surface of the catheter within which the marking material is deposited. The mechanical keying between the marking material and the catheter improves the adhesion of the marking material. Besides adding to the cost of producing a catheter, however, such grooves may produce a rougher surface which could increase tissue damage during insertion and removal.

OBJECTS AND SUMMARY OF THE INVENTION

Accordingly, it is an object of the invention to provide a radiopaque marking system for a catheter which overcomes the drawbacks of the prior art.

It is a further object of the invention to provide a radiopaque marking system wherein a staff having bands of radiopaque material thereon is sealed within a lumen of a catheter.

It is a further object of the invention to provide a catheter for stereotaxic treatment including a plurality of lumens disposed parallel to a longitudinal axis thereof. A staff having bands of radiopaque material thereon is sealed into one of the lumens.

Briefly stated, the present invention provides a stereotaxic catheter having at least one lumen parallel to an axis thereof. The lumen includes a staff having disposed thereon or therein a predetermined number of spaced-apart markings of a radiopaque material. In a preferred embodiment, the markings are equidistantly spaced circumferential bands of a material having a large X-ray signature. The lumen containing the staff is preferably sealed at both ends and is most preferably sealed in close adjacency to each end of the staff whereby the staff is retained in a stable and predictable positional relationship to the remainder of the catheter.

According to an embodiment of the invention, there is provided a radiopaque marking system for a catheter, wherein the catheter includes at least one lumen parallel to an axis thereof, comprising: a staff in the at least one lumen, a least one body of a radiopaque material on the staff, and means for sealing the staff within the lumen, whereby the radiopaque material is isolated from an exterior of the catheter.

According to a feature of the invention, there is provided a stereotaxic catheter comprising: a catheter body, the catheter body including means for permitting the insertion thereof into tissue, at least one lumen in the catheter body, and generally parallel to an axis thereof, a staff in the at least one lumen, at least one band of a radiopaque material on the staff, the band being disposed in a location on the staff where it is carried into the tissue when the catheter body is inserted into the tissue, whereby a radiopaque marker is provided within the tissue visible on an X-ray image, means for sealing the staff in the at least one lumen, whereby the radiopaque material is isolated from the tissue, and the means for sealing including means for maintaining a stable positional relationship between said staff and a remainder of the catheter, whereby the radiopaque marker has a predetermined positional relationship to the remainder of the catheter.

The above, and other objects, features and advantages of the present invention will become apparent from the following description read in conjunction with the accompanying drawings, in which like reference numerals designate the same elements.

BRIEF DESCRIPTION OF THE DRAWINGS

FIG. 1 is a side view of a stereotaxic catheter including bands of radiopaque material according to the prior art.

FIG. 2 is a cross section taken along II—II in FIG. 1.

FIG. 3 is a side view of a stereotaxic catheter including a radiopaque marking system according to an embodiment of the invention.

FIG. 4 is an enlarged view of the banded staff of FIG. 3.

DETAILED DESCRIPTION OF THE PREFERRED EMBODIMENT

Referring to FIG. 1, there is shown, generally at 10, a stereotaxic catheter of a type disclosed in the foregoing referenced patent application. The figure is labelled prior art solely because stereotaxic catheter 10 corresponds to the disclosure of the referenced patent application, commonly assigned with the present application, and which has co-pendency with the present application. Such labelling should not be taken to signify an admission that the matter contained in the figure and described in the following constitutes admitted prior art for any purpose beyond providing a background environment to enhance an understanding of the present disclosure.

A catheter body 12 includes a cylindrical portion 14 having a conical tip 16 at its lower end. A central lumen 18 axially disposed in catheter body 12 may include an open lower end 20 to permit the introduction of drugs or the removal of biopsy specimens through catheter body 12. A plurality of side lumens 22, 24 and 26 (See also FIG. 2) are disposed about central lumen 18. Side lumens 22, 24 and 26 are closed at their bottom ends and open at their top ends to permit the entry therein of connections such as, for example, wires 28 and 30 which, in the referenced allowed patent application, include a coaxial cable leading to a microwave antenna (not shown) in one side lumen and connectors for a thermistor (not shown) in another side lumen. A cap 32 at an upper end of stereotaxic catheter 10 seals about wires 28 and 30 at the upper ends of side lumens 22, 24 and 26. An opening (not shown) may be provided aligned with central lumen 18 for access to tissue in the vicinity of open lower end 20.

A plurality of radiopaque bands 34, 36, 38, 40 and 42 are disposed equidistantly spaced along an axis on the surface of cylindrical portion 14. As noted in the description of the background of the invention, maintaining radiopaque bands on such a surface, especially during abrasion incident to insertion and removal of stereotaxic catheter 10 in brain tissue presents a problem.

Referring now to FIGS. 3 and 4, there is shown, generally at 44, a stereotaxic catheter according to an embodiment of the invention. Side lumen 24 contains a calibration staff 46 having a plurality of radiopaque bands 48, 50, 52, 54 and 56 equidistantly spaced along an axis thereof. A lower end 58 and a upper end 60 are sealed either abutting, or closely spaced from adjacent ends of calibration staff 46 whereby calibration staff 46 is prevented from substantial longitudinal displacement within side lumen 24. Accordingly, longitudinal positions of radiopaque bands 48-56 are precisely and stably established for aiding in the precision with which they are capable of indicating the positions of elements in stereotaxic catheter 44.

Several desirable consequences and opportunities flow from sealing calibration staff 46 within side lumen 24. First, since calibration staff 46 remains out of contact with the patient, it may be made of a material more hospitable to retaining the radiopaque marking material thereon. Calibration staff 46 is preferably formed of a suitable plastic material such as, for example, polyvinyl chloride. Other suitable plastic or metal materials may be employed. The surface of calibration staff 46 may be roughened, or otherwise treated, to improve mechanical keying of the marking material. Deposition of the material forming radiopaque bands 48-56 within the brain tissue is prevented. Since the likelihood of the material of radiopaque bands 48-56 being deposited within living tissue is eliminated, additional materials may be considered for forming them. For example, a paste containing tantalum powder has a suitable X-ray signature but is not desirable for use where it may remain in the tissue. In a sealed environment, such as provided in the present invention, a tantalum-containing material may be employed without danger to the patient.

In a suitable installation, two or more calibration staffs 46 may be sealed in an equal number of side lumens. In addition, although the foregoing disclosure employs a radiopaque coating on an exterior surface of calibration staff 46, an embodiment of the invention in which the radiopaque material is incorporated within calibration staff 46 should be considered to remain within the scope of the invention. One technique could include scoring lines about the circumference of calibration staff 46 to contain the radiopaque marking material. Other techniques would occur to one skilled in the art.

Having described preferred embodiments of the invention with reference to the accompanying drawings, it is to be understood that the invention is not limited to those precise embodiments, and that various changes and modifications may be effect ed therein by one skilled in the art without departing from the scope or spirit of the invention as defined in the appended claims.

What is claimed is:

1. A radiopaque marking system for a cathether, wherein said catheter includes at least one lumen parallel to an axis thereof, comprising:

said at least one lumen including a first length;

a staff in said at least one lumen;

said staff being a radiotransparent material;

at least first and second bands of a radiopaque material axially spaced a predetermined distance apart on said staff;

said staff including a second length;

said second length being substantially equal to said first length, whereby said staff is disposed in a known position within said lumen;

said at least first and second bands having a known positional relationship along a length of said staff, whereby said at least first and second bands also have a known positional relationship along a length of said catheter; and means for sealing said staff within said lumen, whereby said radiopaque material is isolated from an exterior of said catheter.

2. A radiopaque marking system according to claim 1 wherein said staff is of a material hospitable to adherence of said radiopaque material.

3. A radiopaque marking system according to claim 2 wherein said staff is a plastic resin.

4. A radiopaque marking system according to claim 3 wherein said plastic resin includes a polyvinyl chloride.

5. A sterotaxic catheter comprising:
a catheter body;
said catheter body including means for permitting the insertion thereof into tissue;
at least one lumen in said catheter body, and generally parallel to an axis thereof;
a staff of radiotransparent material in said at least one lumen;
at least first and second bands of a radiopaque material axially spaced a predetermined distance apart on said staff, at least said first band being disposed in a location on said staff where it is carried into said tissue when said catheter body is inserted into said tissue, whereby a radiopaque marker is provided within said tissue visible on an X-ray image;
means for sealing said staff in said at least one lumen, whereby said radiopaque material is isolated from said tissue;
said at least one lumen having a first length;
said staff having a second length; and
said first and second lengths being related to retain said staff in a predetermined longitudinal position in said at least one lumen, whereby said first and second bands have predetermined positional relationships to said remainder of said catheter.

* * * * *

UNITED STATES PATENT AND TRADEMARK OFFICE
CERTIFICATE OF CORRECTION

PATENT NO. : 4,796,637

DATED : January 10, 1989

INVENTOR(S) : Frank Mascuch, Arthur Winter, Satish Laroia

It is certified that error appears in the above-identified patent and that said Letters Patent is hereby corrected as shown below:

On cover page, Inventors should read:

-- Frank Mascuch, Watchung; Arthur Winter, Short Hills; Satish Laroia, Edison; all of New Jersey --

Signed and Sealed this

Twenty-sixth Day of November, 1991

*Attest:*

HARRY F. MANBECK, JR.

*Attesting Officer*  *Commissioner of Patents and Trademarks*